(12) United States Patent
Luxembourg et al.

(10) Patent No.: US 7,304,163 B2
(45) Date of Patent: Dec. 4, 2007

(54) BENZOTRIAZOLE-1-YL-N-OXY PHOSPHONIUM COUPLING AGENT

(75) Inventors: Yoav Luxembourg, Kfar-Shemaryahu (IL); Youval Shvo, Arsuf (IL); Ariel Ewenson, Omer (IL)

(73) Assignee: Luxembourg Industries Ltd., Tel-Aviv (IL)

( * ) Notice: Subject to any disclaimer, the term of this patent is extended or adjusted under 35 U.S.C. 154(b) by 83 days.

(21) Appl. No.: 10/551,522

(22) PCT Filed: Aug. 16, 2005

(86) PCT No.: PCT/IL2005/000886

§ 371 (c)(1),
(2), (4) Date: Sep. 30, 2005

(87) PCT Pub. No.: WO2007/020620

PCT Pub. Date: Feb. 22, 2007

(65) Prior Publication Data

US 2007/0043207 A1  Feb. 22, 2007

(51) Int. Cl.
*C07F 9/6518* (2006.01)
(52) U.S. Cl. ........................ 548/257; 548/112; 530/333
(58) Field of Classification Search ................ 548/257, 548/111; 546/20; 530/333
See application file for complete search history.

(56) References Cited

OTHER PUBLICATIONS

Albericio et al. "On the Use of PyAOP, A Phosphonium Salt Derived From HOAt, in Solid-Phase Peptide Synthesis", Tetrahedron Letters, 38(27): 4853-4856, 1997.
Carpino et al. "1-Hydroxy-7-Azabenzotriazole. An Efficent Peptide Coupling Additive", Journal of the American Chemical Society, 115: 4397-4398, 1993.
"IUPAC-IUB Commission on Biochemical Nomenclature Symbols for Amino-Acid Derivatives and Peptides Recommendations (1971)", The Journal of Biological Chemistry, 247(4):977-983, 1972.
Ueki et al. "A New One-Pot Method for Fmoc Solution Synthesis", Peptides, Proceedings of the 25th European Peptide Symposium, Akademiai Kiado, Budapest, p. 252-253, 1998.
Coste et al. "PyBOP®: A New Peptide Coupling Reagent Devoid of Toxic By-Product", Tetrahedron Letters, 31(2): 205-208, 1990.
Albericio et al. "Coupling Methods: Solid-Phase Formation of Amide and Ester Bonds", Solid-Pase Synthesis: A Practical Guide, Chap.6: 275-330, 2000.
Vendrell et al. "N-[Chloro(Dimethylamino)Methylene]-N-Methylmethanaminium Chloride (TMUCI CI), the Reagent of Choice for the Solid-Phase Synthesis of Anilidis", Tetrahedron Letters, 46(32): 5383-5386, 2005.
PCT Search Report and Written Opinion PCT/IL05/00886 dated Mar. 22, 2006.

*Primary Examiner*—Kamal A. Saeed
*Assistant Examiner*—Yong Chu (57) ABSTRACT

Novel phosphonium salts of benzotraizoles, which are highly reactive coupling agents, and are particularly useful in peptide synthesis, are disclosed. Further disclosed is a process of preparing the novel phosphonium salts and methods utilizing same for preparing peptides.

8 Claims, 4 Drawing Sheets

Figure 1 (Background Art)

dicyclohexylcarbodiimide (DCC)

1-ethyl-3-(3'-dimethylaminopropyl)carbodiimide (EDC)

N,N'-diisopropylcarbodiimide (DIC)

Figure 2 (Background Art)

1-hydroxybenzotriazole (HOBt)

1-hydroxy-6-chlorobenzotriazole (Cl-HOBt)

1-hydroxy-7-azabenzotriazole (HOAt)

benzotriazole-1-yl-oxy-tris-pyrrolidino-
phosphonium hexafluorophosphate (PyBOP)

7-azabenzotriazole-1-yl-oxy-tris-pyrrolidino-
phosphonium hexafluorophosphate (PyAOP)

Figure 5 tris-(1-pyrrolidine)phosphine oxide tri-pyrrolidin-1-yl-phosphonium chloride tris-(1-pyrrolidino)phosphonium hexaflurophosphate 6-chloro-1-hydroxybenzotriazole (HBOT)

6-chloro-1-hydroxybenzotriazole-tris-(1-pyrrolidino)phosphonium hexafluorophosphate

BENZOTRIAZOLE-1-YL-N-OXY PHOSPHONIUM COUPLING AGENT

RELATED PATENT APPLICATION

This application is a National Phase Application of PCT/IL2005/000886 having International Filing Date of 16 Aug. 2005.

FIELD AND BACKGROUND OF THE INVENTION

The present invention relates to the field of chemical synthesis and, more particularly, to novel coupling agents that can be beneficially utilized in the syntheses of various substances and particularly in peptide synthesis.

All known life forms and life processes are based on proteins which are essential to all biological functions. Consequently, all the illnesses and disorders associated with life involve proteins. Among many other functions, proteins play a key role in signaling pathways of immunological and/or neurological processes and thus they are major players in many congenital, chronic and infectious diseases and disorders.

As such, proteins exhibit highly potent therapeutic efficacy and therefore attract a great pharmaceutically-focused attention, especially in the post-genomic and proteomic era, where important advances in molecular biology and gene technology are bringing significant changes in biomedical sciences. The elucidation of the human genome, followed by advancements in functional genomics and proteomics, revolutionized the understanding of the detailed molecular mechanisms, underlying a broad spectrum of peptide and protein related diseases and disorders. As a result, novel therapeutic targets have been identified and novel mechanism-based therapeutic paradigms have been suggested, whereby peptides play a key role in all of these transitions.

Consequently there has been a notable increase in researches, both academic and industrial, which are aimed at developing novel peptide-based drugs. From a pharmaceutical market point of view, peptides are presently considered as active pharmaceutical ingredients (API) that can be used in a variety of therapeutic applications and particularly as, for example, antibiotics, hormones, immunomodulators, anti-angiogenesis agents, therapeutic agents for treating CNS and other neurological disorders, analgesics, anti-obesity drugs, and as therapeutic agents for treating immune disorders such as allergy, asthma, hemophilia, anemia and autoimmune diseases [Loffet, A. 2002, *J Peptide Sci.* 8, 1].

However, although peptides have enormous therapeutic potential, their widespread use has been limited by several restrictive technical factors. Today, manufacturing companies face the unprecedented challenge of producing hundred kilograms to tons quantities of complex peptides. Such a massive production typically uses expensive and complex modern technologies, rendering peptide manufacture difficult and cost-inefficient as compared with other pharmaceuticals. Large-scale manufacturing and purification of peptides in a bioactive form can therefore be a limiting step in the commercialization of peptide-based drugs.

A key step in the peptide production process is the formation of the peptide bond (an amide bond formed between the carboxylic acid group of one amino acid and the amine group of another amino acid). In peptide syntheses, formation of a peptide bond typically requires the activation of the carboxylic acid, which usually involves the use of a peptide coupling agent [for a comprehensive review on peptide coupling agents see, F. Albericio, S. A. Kates, Solid-Phase Synthesis: A Practical Guide, S. A. Kates, F. Albericio Eds; Marcel Dekker, New York, N.Y., 2000, pp. 273-328 and F. Albericio, R. Chinchilla, D. J. Dodsworth, C. Najera, 2001, *Org Prep. Proc. Int.*, 33, 202].

Although the synthesis of medium-large peptides for basic research is a well established procedure, the combination of the 20 naturally occurring amino acids and a growing number of unnatural amino acids makes each peptide synthesis unique at the industrial level, oftentimes requiring closer attention to each amino acid coupling. Some of the rules for coupling agents validated in the research scale can be applied at industrial level, but the results are still hardly predictable.

Figure 1:
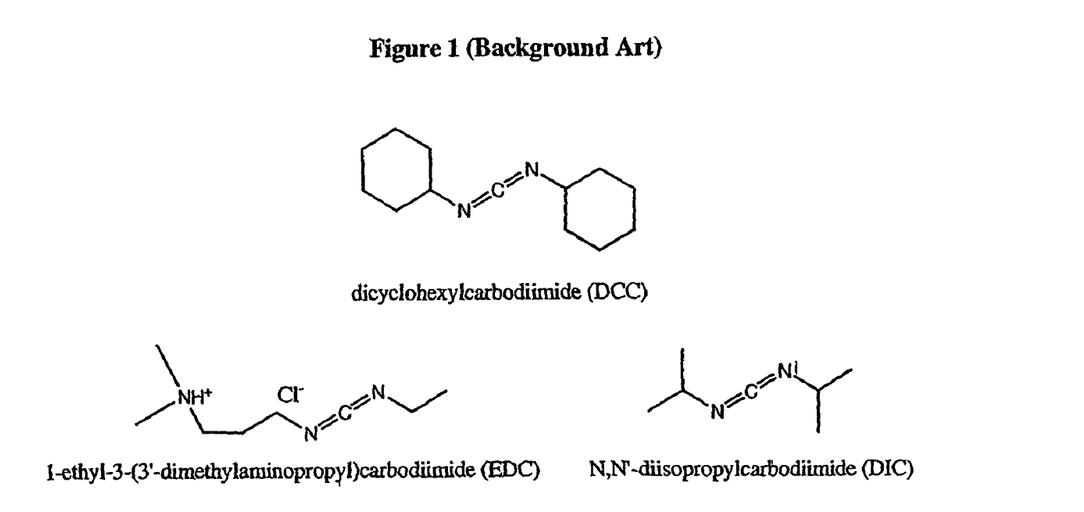
FIG. 1 presents the chemical structures of background art coupling agents of the carboiimide family: dicyclohexylcarbodiimide (DCC), 1-ethyl-3-(3'-dimethylaminopropyl)carbodiimide (EDC) and N,N'-diisopropylcarbodiimide (DIC)

Thus use of peptide coupling agents in the industry has started as early as 1955 with the introduction of dicyclohexylcarbodiimide (DCC) [Sheehan, J. C. and Hess, G. P., 1955, *J. Am. Chem. Soc.*, 77, 1067], which at that time was already known and well studied as a reagent for formation of amide bond [Khorana, H. G., 1952, *J. Chem. Soc.*, 2081]. The chemical structures of DCC, as well as of 1-ethyl-3-(3'dimethylaminopropyl)carbodiimide (EDC) and N,N'-diisopropylcarbodiimide (DIC), other coupling agents of the carboiimide family, are presented in FIG. 1.

Carbodiimides are indeed the most available and low-cost coupling agents amongst the presently known reagents. The primary reactive species, O-acylisourea, is one of the most reactive species for peptide coupling. Shortcomings associated with the use of carbodiimides as coupling agents therefore mostly stem from the high and relatively incontrollable reactivity thereof and include, for example, racemization, side reactions and low yields due to the formation of the poorly active N-acyl urea. Furthermore, while low dielectric constant solvents such as $CHCl_3$ or $CH_2Cl_2$ are optimal for carbodiimides, the use of these solvents precludes the use of automatic solid-phase synthesis machines, and thus, carboiimides coupling agents can be used, at most, in manual or semi-automatic modes. Carbodiimides are also incompatible with Fmoc/t-Bu solid-phase chemistry, because the urea derivative formed in such syntheses is typically not soluble in common solvents. Such urea derivatives are also difficult to remove in solution chemistry.

Figure 2:
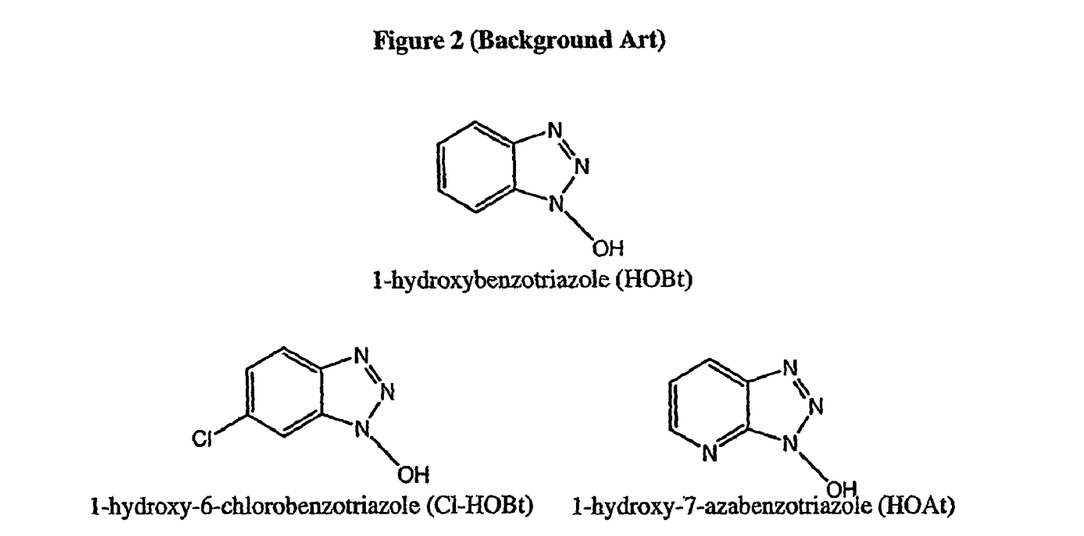
FIG. 2 presents the chemical structures of background art benzotriazole derivatives serving as additives to the coupling agents of the carbodiimide family: 1-hydroxybenzotriazole (HOBt), 1-hydroxy-6-chlorobenzotriazole (Cl-HOBt) and 1-hydroxy-7-azabenzotriazole (HOAt)

At the beginning of the 70's, 1-hydroxybenzotriazole (HOBt) [König, W., Geiger, R., 1970, Chem. Ber. 103, 788 and 2034] was proposed as an additive to DCC. The addition of HOBt was aimed at reducing the racemization associated with DCC coupling. The relative success of this additive signaled the beginning of a period during which other benzotriazole derivatives such as 1-hydroxy-56-chlorobenzotriazole (Cl-HOBt) [Ueki, M. and Yanagihira, T., Peptides 1998, *Proceedings of the 25th European Peptide Symposium*, S. Bajusz, F. Hudecz Eds, Akademiai Kiado, Budapest, p. 252] and 1-hydroxy-7-azabenzotriazole (HOAt) [Carpino, L. A., 1993, *J. Am. Chem. Soc.*, 115, 4397] have been developed and successfully used (see, FIG. 2). During the past years the addition of benzotriazole derivatives as additives to DCC and other carbodiimides became almost mandatory to preserve the peptide bond formation by carbodiimide activation of low yields and undesired side reactions and loss of chirality.

In the last decade, the use of phosphonium and aminium/uronium salts, referred to herein in short as "onium salts", of hydroxybenzotriazole derivatives as peptide coupling agents, has been introduced. Although these reagents have been rapidly adapted for research purposes, only a few of them have been found compatible with current industrial requirements and synthetic strategies and were adopted by the industry.

Figure 3:
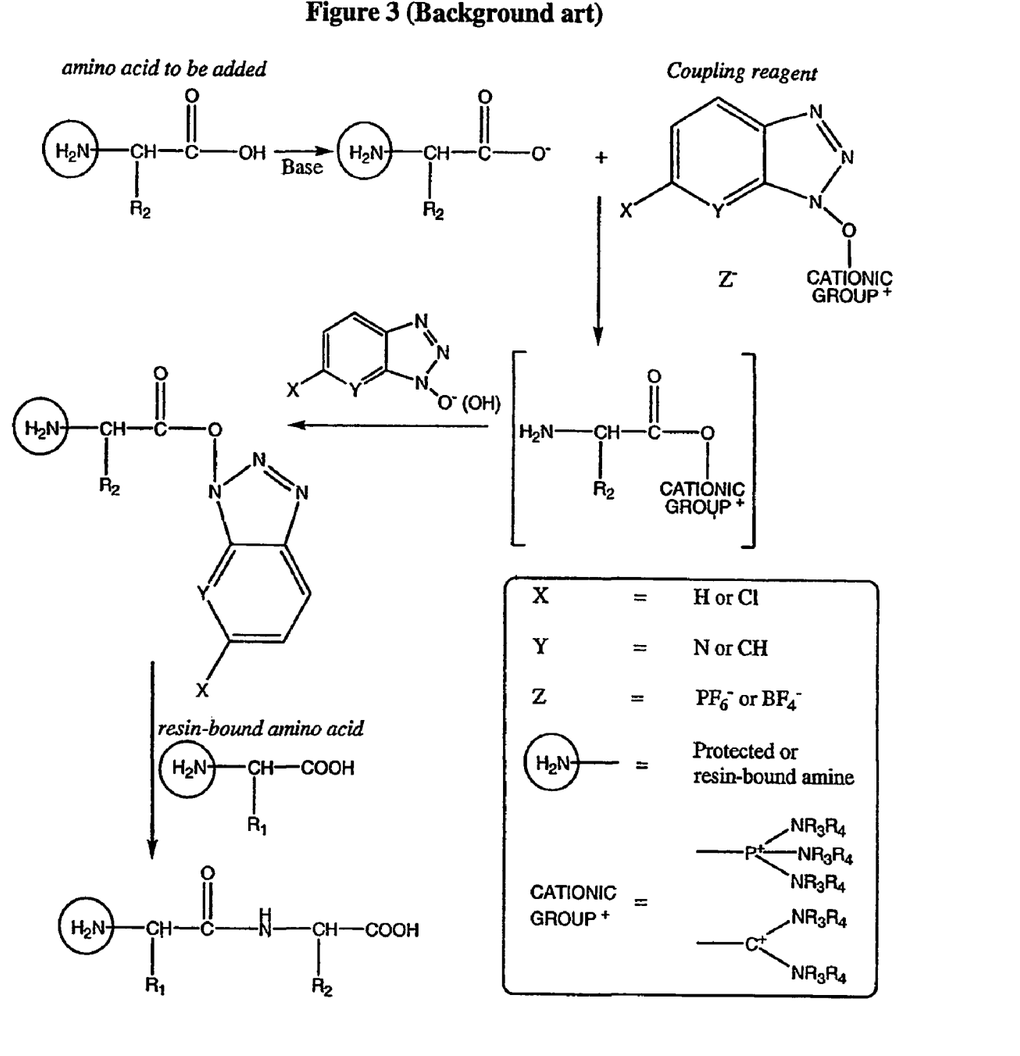
FIG. 3 presents a scheme illustrating the proposed mechanism of peptide synthesis by coupling agent of the aminium and phosphonium salt families.

The species that reacts with onium salts is the carboxylate of the amino/organic acid. Therefore, performing the coupling reaction in the presence of at least one equivalent of a base is essential while using these reagents. The mechanism by which these "onium" salts acts as coupling agents is schematically illustrated in FIG. 3.

The presently most reactive aminium salt coupling agent is 2-(7-aza-1H-benzotriazole-1-yl)-1,1,3,3-tetramethyluronium hexafluorophosphate (HATU) [Carpino, L. A., 1993, *J. Am. Chem. Soc.*, 115, 4397]. The chemical structures of HATU and analogs thereof are presented in Scheme 1 below.

SCHEME 1

| | X | Y | Z |
|---|---|---|---|
| HATU | H | N | $PF_6$ |
| HBTU | H | CH | $PF_6$ |
| TBTU | H | CH | $BF_4$ |
| HCTU | Cl | CH | $PF_6$ |
| TCTU | Cl | CH | $BF_4$ |

However, the use of the aminium salts as peptide coupling agents was found to be limited in various aspects. First, during the activation of hindered carboxylic components, such as those involved in cyclization reactions of hindered amino acids, the aminium salts can react with a more available amino component, leading to a guanidine derivative, a process that terminates the peptide chain. Furthermore, it has been discovered that aminium salts can contain traces of dimethylamine, which can also react with the carboxylic component to give the corresponding dimethylamide. Finally, HATU as well as its less reactive analogues (see, Scheme 1 above) are prohibitively expensive, rendering their industrial use impractical.

Figure 4:
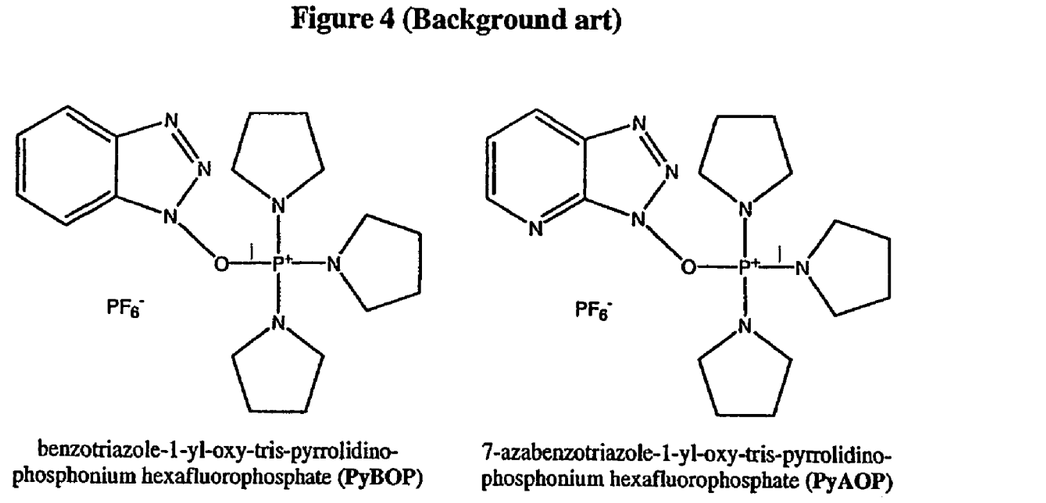
FIG. 4 presents the chemical structures of two exemplary coupling agents of the phosphonium salts family: benzotriazole-1-yl-oxy-tris-pyrrolidino-phosphonium hexafluorophosphate (PyBOP) and 7-azabenzotriazole-1-yl-oxy-tris-pyrrolidino-phosphonium hexafluorophosphate (PyAOP)

The most prevalent phosphonium salts of benzotriazoles that are presently used as peptide coupling agents are benzotriazol-1-yl-N-oxy-tris(pyrrolidino)phosphonium hexafluorophosphate (PyBOP) [Coste, J. et al., 1975, *Tetrahedron Lett.*, 31, 205] and the later uncovered 7-azabenzotriazol-1-yl-N-oxy-tris(pyrrolidino)phosphonium hexafluorophosphate (PyAOP) [Albericio, F. et al., 1997, *Tetrahedron Lett.*, 38, 4853], which is derived from HOAt and is presently considered as the most reactive phosphonium salt (see, FIG. 4). PyBOP and PyAOP, are specifically useful as coupling agent in cyclization steps or for the activation of hindered amino acids, where the use of aminium salts can lead to the formation of guanidine derivatives. Since it was found that PyBOP and PyAOP do not terminate the peptide chain, these coupling agents can be used in excess and be added during the coupling step, while circumventing the risk of chain termination.

Thus, the presently known peptide coupling agents are typically limited by their low desired reactivity, side products formed thereby and/or high cost.

Due to the ongoing developments of peptide-based drugs and the limitations associated with the presently known peptide coupling agents, there is a widely recognized need, and it would be highly advantageous to have novel, efficient peptide coupling agent devoid of the above limitations.

It is noteworthy that coupling agents that are useful in peptide synthesis can also be used in other organic syntheses that require activation of a carboxylic moiety. Such syntheses can be used to produce organic compounds of biological interest such as, for example, peptoids, oligocarbamates, oligoamides, β-lactams, esters, polyenamides, benzodiazepines, diketopiperazines, and hydantoins.

SUMMARY OF THE INVENTION

In a search for a novel peptide coupling agent, the present inventors have designed, prepared and successfully practiced a novel coupling agent which is more effective than commonly used coupling agents, simple to produce and use in modern peptide synthesis techniques.

Thus, according to one aspect of the present invention there is provided a coupling agent comprising 6-chloro-1-hydroxybenzotriazol-1-yl-N-oxy-tris(pyrrolidino)phosphonium hexafluorophosphate.

According to another aspect of the present invention there is provided a process of preparing 6-chloro-1-hydroxybenzotriazol-1-yl-N-oxy-tris(pyrrolidino)phosphonium hexafluorophosphate, which comprises providing tris-(1-pyrrolidino)phosphonium hexafluorophosphate; providing 6-chloro-1-hydroxybenzotriazole; and reacting the tris-(1-pyrrolidino)phosphonium hexafluorophosphate and the 6-chloro-1-hydroxybenzotriazole.

According to further features in preferred embodiments of the invention described below, the reaction between tris-(1-pyrrolidino)phosphonium hexafluorophosphate and the 6-chloro-1-hydroxybenzotriazole is performed in the presence of a base and an organic solvent.

According to still further features in the described preferred embodiments providing the tris-(1-pyrrolidino)phosphonium hexafluorophosphate includes providing tris-(1-pyrrolidine)phosphine oxide; converting the tris-(1-pyrrolidine)phosphine oxide to tri-pyrrolidin-1-yl-phosphonium chloride; and reacting the tri-pyrrolidin-1-yl-phosphonium chloride with potassium hexafluorophosphate.

According to still further features in the described preferred embodiments the 6-chloro-1-hydroxybenzotriazol-1-yl-N-oxy-tris(pyrrolidino)phosphonium hexafluorophosphate is obtained in a purity that is equal to or is greater than 96%.

According to yet another aspect of the present invention there is provided a method of synthesizing a peptide. The method, according to this aspect of the present invention, comprises sequentially reacting a plurality of amino acids, one with the other, in the presence of 6-chloro-1-hydroxybenzotriazol-1-yl-N-oxy-tris(pyrrolidino)phosphonium hexafluorophosphate According to further features in preferred embodiments of the invention described below, at least one of the amino acids is selected from the group consisting of an amino acid having a secondary alpha amine, an amino acid having a tertiary alpha amine, an amino acid having a substituted alpha carbon atom and an amino acid having an amino-containing side chain.

According to still further features in the described preferred embodiments at least one of the amino acids is selected from the group consisting of an amino acid having a secondary alpha amine and an amino acid having a tertiary alpha amine.

According to still further features in the described preferred embodiments such a peptide is obtained in a yield greater than 10%.

According to still further features in the described preferred embodiments at least one of the amino acids is an amino acid having a substituted alpha carbon atom.

According to still further features in the described preferred embodiments at least two coupled amino acids in the peptide are amino acids having a substituted alpha carbon atom.

According to still further features in the described preferred embodiments the alpha carbon is substituted by an alkyl.

According to still further features in the described preferred embodiments such a peptide is obtained in a yield greater than 90%.

According to still further features in the described preferred embodiments at least one of the amino acids is an amino acid having an amino-containing side chain.

According to still further features in the described preferred embodiments at least two coupled amino acids in the peptide are amino acids having an amino-containing side chain.

According to still further features in the described preferred embodiments the amino acid having an amino-containing side chain is arginine.

According to still further features in the described preferred embodiments such a peptide is obtained in a yield greater than 80%.

According to still further features in the described preferred embodiments synthesizing the peptide is effected by a solid phase synthesis.

According to an additional aspect of the present invention there is provided a crude composition of peptides, which are synthesized in a C-terminus to N-terminus direction, the composition consisting essentially of a peptide having a desired amino acid sequence and a plurality of peptides having undesired amino acid sequences and being impurities to the peptide having the desired amino acid sequence, wherein a concentration of the peptide having the desired amino acid sequence in the composition is at least 5% above a concentration of an identical peptide having the desired amino acid sequence in a composition of peptides being synthesized in the C-terminus to N-terminus direction using benzotriazol-1-yl-N-oxy-tris(pyrrolidino)phosphonium hexafluorophosphate as a coupling agent otherwise prepared under identical conditions.

According to further features in preferred embodiments of the invention described below, the peptide having the desired amino acid sequence comprises at least one amino acid residue selected from the group consisting of a residue of an amino acid having a secondary alpha amine, a residue of an amino acid having a tertiary alpha amine, a residue of an amino acid having a substituted alpha carbon, atom and a residue of an amino acid having an amino-containing side chain.

According to still further features in the described preferred embodiments the peptide having the desired amino acid sequence comprises at least two coupled amino acid residues, whereby at least one of the at least two amino acid residues is selected from the group consisting of a residue of an amino acid having a secondary alpha amine and a residue of an amino acid having a tertiary alpha amine.

According to still further features in the described preferred embodiments the amino acid having a secondary alpha amine is N-methylvaline.

According to still further features in the described preferred embodiments the peptide having the desired amino acid sequence comprises at least two coupled amino acid residues acids having a substituted alpha carbon atom.

According to still further features in the described preferred embodiments the alpha carbon atom is substituted by an alkyl.

According to still further features in the described preferred embodiments the amino acid residue having the substituted alpha carbon atom is an amino isobutyric acid (aib) residue.

According to still further features in the described preferred embodiments the peptide having the desired amino acid sequence comprises at least two coupled amino acid residues acids having an amino-containing side chain.

According to still further features in the described preferred embodiments the amino acid residue having an amine-containing side chain is an arginine residue.

According to still further features in the described preferred embodiments the crude composition of peptides is in a form selected from the group consisting of a powdered composition, a lyophilized composition, a composition bound to a solid support, a solubilized composition and a dissolved composition.

According to yet another aspect of the present invention there is provided a compound having the general formula I:

Formula I wherein X is a halogen substituent; Y is selected from the group consisting of CR' and nitrogen; Z is an inorganic anion; $R_1$-$R_6$ are each independently selected from the group consisting of hydrogen, alkyl, cycloalkyl and aryl, or, alternatively, at least one of $R_1$ and $R_2$, $R_3$ and $R_4$ and $R_5$ and $R_6$ forms a five- or six-membered carbocyclic ring; and R' is selected from the group consisting of hydrogen, alkyl and cycloalkyl. According to further features in preferred embodiments of the invention described below, the compound having the general Formula I is a coupling agent that can be beneficially utilized in peptide synthesis.

According to still further features in the described preferred embodiments the halogen atom is chloride.

According to still further features in the described preferred embodiments each of $R_1$ and $R_2$, $R_3$ and $R_4$ and $R_5$ and $R_6$ forms a five- or six-membered carbocyclic ring, and preferably forms a five-membered carbocyclic ring.

According to still further features in the described preferred embodiments the anion is selected from the group consisting of hexahalophosphate, tetrahaloborate, trihalomethanesulfonate and bis(trihalomethylsulfonyl)imide, and preferably the anion is hexafluorophosphate.

According to yet another aspect of the present invention there is provided a process of preparing the compound having the general Formula I, the process comprises: providing a compound having the general Formula II:

Formula II wherein R₁-R₆ are each independently selected from the group consisting of hydrogen, alkyl, cycloalkyl and aryl, or, alternatively, at least one of R₁ and R₂, R₃ and R₄ and R₅ and R₆ forms a five- or six-membered carbocyclic ring; and Z is selected from the group consisting of halide, hexahalophosphate, terahaloborate, trihalomethanesulfonate and bis(trihalomethylsulfonyl)imide; providing a compound having the general Formula III:

Formula III wherein X is a halogen atom and preferably a chloride; Y is selected from the group consisting of CR' and nitrogen; and T is selected from the group consisting of hydrogen, alkyl, and cycloalkyl; and reacting the compound having the general Formula II and the compound having the general Formula III, thereby obtaining the compound having general Formula I.

According to still further features in the described preferred embodiments the reaction is performed in the presence of a base and an organic solvent.

According to still further features in the described preferred embodiments each of R₁ and R₂, R₃ and R₄ and R₅ and R₆ forms a five- or six-membered carbocyclic ring, and preferably each of said R₁ and R₂, R₃ and R₄ and R₅ and R₆ forms a five-membered carbocyclic ring.

According to still further features in the described preferred embodiments the anion is selected from the group consisting of hexahalophosphate, tetrahaloborate, trihalomethanesulfonate and bis(trihalomethylsulfonyl)imide, and preferably the anion is hexafluorophosphate.

According to still further features in the described preferred embodiments providing the compound having the general Formula II includes providing a compound having general Formula IV:

Formula IV wherein W is selected from the group consisting of oxygen and sulfur; converting the compound having the general Formula IV to a phosphonium halide salt thereof; and reacting the phosphonium halide with Z, thereby obtaining the compound having the general Formula II.

According to still further features in the described preferred embodiments the compound having general Formula I is 6-chloro-1-hydroxybenzotriazol-1-yl-N-oxy-tris(pyrrolidino)phosphonium hexafluorophosphate (PyClock).

According to yet another aspect of the present invention there is provided a method of preparing a peptide, the method comprising sequentially reacting a plurality of amino acids, one with the other, in the presence of the compound having the general Formula I.

According to yet another aspect of the present invention there is provided a use of the compound having the general Formula I as a coupling agent for preparing a peptide.

According to further features in preferred embodiments of the above aspect, the peptide is obtained in a yield that ranges from 80% to 97%.

The present invention successfully addresses the shortcomings of the presently known configurations by providing novel peptide coupling agents which exhibit superior performance as compared with the presently known coupling agents.

As used herein, the singular form "a", "an" and "the" include plural references unless the context clearly dictates otherwise. For example, the term "a protein" or "at least one protein" may include a plurality of proteins, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range to such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the term "comprising" means that other steps and ingredients that do not affect the final result can be added. This term encompasses the terms "consisting of" and "consisting essentially of".

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein throughout, the following abbreviations are used:
BOP for Benzotriazole-1-yl-oxy-tris-(dimethylamino)-phosphonium hexafluorophosphate;
Cl-HOBt for 6-chloro-1-hydroxybenzotriazole;
DCC for N,N'-dicyclohexylcarbodiimide, dicyclohexylcarbodiimide;
DIBOC for di-t-butyl dicarbonate;
DIC for 1,3-Diisopropylcarbodiimide;
DIEA for N,N-Diisopropylethylamine;
DIP or DIPCDI DIC for N,N'-diisopropylcarbodiimide;

DMAP for 4-Dimethylaminopyridine;
DMF for N,N-dimethylormamide;
EDC for 1-ethyl-3-(3'-dimethylaminopropyl)carbodiimide;
EDC HCl for 1-(3-Dimethylaminopropyl)-3-ethyl-carbodiimide hydrochloride;
Fmoc for 9-fluorenylmethoxycarbonyl;
HAUT for 2-(7-Aza-1H-benzotriazole-1-yl)-1,1,3,3-tetramethyluronium hexafluorophosphate;
HBTU for 2-(1H-Benzotriazole-1-yl)-1,1,3,3-tetramethyluronium hexafluorophosphate or N-[(1H-benzotriazol-1-yl)(dimethylamino)methylene]-N—
HCTU, N-[(1H-6-chlorobenzotriazol-1-yl)(dimelhylamino)methylene]
HOAt for 1-hydroxy-7-azabenzotriazole;
HOBt for 1-hydroxybenzotriazole;
HPTU for N-[(dimethylamino)-1H-1,2,3-triazolo-[4.5-beta]pyddino-1-ylmethylene]-N-methylmethanaminium hexafluorophosphate;
N-methylmethanaminium hexafluorophosphate N-oxide;
PyAOP for 7-azabenzotriazol-1-yl-N-oxy-tris(pyrrolidino)phosphonium hexafluorophosphate;
PyBOP for benzotriazol-1-yl-N-oxy-tris(pyrrolidino)phosphonium hexafluorophosphate;
TBTU for N-[(1H-benzotriazol-1-yl)(dimethylamino)methylene]-N-methylmethanaminium tetrafluoroborate N-oxide or 2-(1H-Benzotriazole-1-yl)-1,1,3,3-tetramethyluronium tetrafluoroborate;
TCTU, N-[(1H-6-chlorobenzotriazol-1-yl)(dimethylamino)methylene]-N-methylmethanaminium tetrafluoroborate N-oxide;
TFA for trifluoroacetic acid;
TFFH for Fluoro-N,N,N",N"-tetramethylformamidinium hexafluorophosphate; and
TNBSA for trinitrobenzenesulfonic acid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of novel phosphonium salts of benzotriazole, which can be beneficially used as coupling agents in various chemical syntheses and are particularly useful as coupling agents for use in peptide syntheses. The present invention is further of a process of preparing such phosphonium salts and of their use in the preparation of peptides.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed in detail hereinabove, the ability to controllably and efficiently form carboxylic bonds such as amide and ester bonds while maintaining safety and cost effectiveness is of the outmost importance for the pharmaceutical and chemical industry. This important task is typically made possible by the use of a coupling agent, which activates the carboxylic acid moiety that participates in such bond formation. Such a coupling agent therefore plays a key role in the preparation of various compounds of biological and pharmaceutical interest including peptides, peptoids, oligocarbamates, oligoamides, β-lactams, polyenamides, benzodiazepines, diketopiperazines, and hydantoins.

While many coupling agents are known, only few can be efficiently utilized in industrial manufacture of such molecules of interest.

In order to provide an optimal coupling agent which is suitable for use in industrial manufacturing, a coupling agent has to be chemically efficient, cost efficient and safe for use. To this end, several criteria must be met, as follows:

Chemical effectiveness: a coupling agent has to be reactive with a wide variety of substrates; reactive in stoichiometric quantities; reactive in both solution and solid-phase synthesis; soluble in typical industrial solvents even at high concentrations; stable in solution for several days at room temperature; simply monitored during the coupling reaction;

prone to only few side reactions; simple to purify from its secondary products after coupling, (e.g., by solvent extraction), and further has to exhibit a high conversion rate at mild conditions (e.g., room temperature, atmospheric pressure and mild pH).

Cost-effectiveness and safety: a coupling agent has to be readily prepared from conventional, safe and readily available raw materials, solvents and/or catalysts; and by well established synthetic technology which does not require installation of sophisticated equipment and which is suitable for industrial up-scaling.

The preparation and use of a coupling agent should be characterized by an effective waste management, which does not generate hazardous waste and can be disposed with low pollution risk.

A coupling agent should have prolonged shelf-life at ambient conditions; be safe for the manufacturer, user and the environment; be non-toxic, non-corrosive and not self-reactive; and be stable with relatively low sensitivity to friction, spark, and electrostatic discharge, particularly during transportation and subsequent storage.

As is further discussed in detail hereinabove, the presently available coupling agents that are used in peptide syntheses suffer several disadvantages, ranging, for example, from chemical inefficiency in terms of side products and low coupling aptitude and yield, and low compatibility with modern automatic and semi-automatic solid-phase peptide-synthesizing techniques to production, maintenance and waste disposal costs.

In a search for such an optimal coupling agent which would address the abovementioned synthetic performance requirements and would overcome the limitations associated with the presently known coupling agents, the present inventors have designed and successfully prepared a novel coupling agent, which combines a selective reactive aptitude at mild condition while maintaining a long shelf-life, safety of use at scaled-up quantities and waste management considerations. As is demonstrated in the Examples section that follows, this novel coupling agent was readily prepared in high yield and purity, and was found highly reactive as a coupling agent when utilized in peptide syntheses.

Thus, according to one aspect of the present invention there is provided a novel coupling agent, which comprises 6-chloro-1-hydroxybenzotriazol-1-yl-N-oxy-tris(pyrrolidino)phosphonium hexafluorophosphate, (abbreviated and is referred to herein interchangeably as PyClock).

6-chloro-1-hydroxybenzotriazol-1-yl-N-oxy-tris(pyrrolidino)phosphonium hexafluorophosphate (PyClock)

As used herein throughout, the phrase "coupling agent", which is also referred to herein interchangeably as "coupling reagent", describes a compound that facilitates the bond formation between a carboxylic functional group and a chemically compatible moiety, by activating the carboxylic functional group.

The phrase "a carboxylic functional group" describes a —C(=D)-E group, where D is oxygen or sulfur and E is, for example, halo, hydroxyl, alkoxy, thioalkoxy and the like.

The term "halo" as used herein refers to fluoro, chloro, bromo or iodo.

The term "hydroxyl" refers to an —OH group.

The term "alkoxy", as used herein, refers to both an —O-alkyl and an —O-cycloalkyl group, as defined herein.

The term "thioalkoxy", as used herein, refers to both an —S-alkyl and an —S-cycloalkyl group, as defined herein.

As used herein, the term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted.

The term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. Chemically compatible moieties that can form a bond with a carboxylic group include, for example, amines, alcohols, thiols, alkyl halides, anhydrides, acyl halides and many other functional groups, as these are defined hereinbelow.

As used herein, the phrase "functional group" describes a chemical group that is capable of undergoing a chemical reaction that typically leads to a bond formation. The bond, according to the present invention, is preferably a covalent bond. Chemical reactions that lead to a bond formation include, for example, nucleophilic and electrophilic substitutions, nucleophilic and electrophilic addition reactions, addition-elimination reactions, cycloaddition reactions, rearrangement reactions and any other known organic reactions that involve a reactive group.

As used herein, the term "amine" refers to an —NR'R" group where R' and R" are each hydrogen, alkyl, alkenyl, cycloalkyl, aryl, heteroaryl (bonded through a ring carbon) or heteroalicyclic (bonded through a ring carbon) as defined hereinbelow. When amines are reacted with carboxylic functional groups, amide bonds are formed.

A "thiol" refers to —SH group. When thiols are reacted with a carboxylic functional groups, thioester bonds are formed.

The term "alkylhalide" refers to alkyl substituted by one or more halogen atoms. When alkylhalides are reacted with a carboxylic functional groups, ester bonds are formed.

The term "acyl halide" describes a —C=O)L group wherein L is a halogen atom, as defined hereinabove. When acyl halides are reacted with a carboxylic functional groups, an anhydride moiety is formed.

The term "alkenyl" refers to an alkyl group which consists of at least two carbon atoms and at least one carbon-carbon double bond.

The term "aryl" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system.

As is demonstrated in the Examples section that follows, PyClock was found to be a highly reactive coupling agent, when used in the preparation of several peptide sequences. More particularly, it has been shown that PyClock is equally a highly effective peptide coupling agent for both naturally occurring and unnatural amino acids and further, that this agent can accomplish the formation of a peptide bond between the less available secondary amine (as in the case, for example, of the unnatural amino acid N-methylvaline), an achievement which was not shared by the presently and widely used peptide coupling agent PyBOP. The synthesis of a pentameric peptide containing the non-standard amino acid 3-amino-2-methyl-propionic acid (Aib) in its sequence reached a remarkable yield of 96.6% with minimal side-products.

PyClock was shown to be an effective peptide coupling agent when used in stoichiometric quantities with respect to the amino-acid during a standard solid-phase peptide synthesis.

The peptide synthesis performed in the presence of PyClock was conducted at room temperature, using mild reagents and standard solvents. Furthermore, the coupling reaction in the presence of PyClock can be easily followed by tracking its breakdown product 6-chloro-1-hydroxybenzotriazole (Cl-HBOT) by simple techniques such as TLC and PHLC.

As discussed and demonstrated hereinbelow, PyClock is prepared at high yield from readily available starting materials, using a simple and cost-effective procedure.

Hence, according to another aspect of the present invention, there is provided a process of preparing 6-chloro-1-hydroxybenzotriazol-1-yl-N-oxy-tris(pyrrolidino)phosphonium hexafluorophosphate (PyClock). The process, according to this aspect of the present invention, is effected by providing tris-(1-pyrrolidino)phosphonium hexafluorophosphate; providing 6-chloro-1-hydroxybenzotriazole (Cl-HBOT); and reacting these two reagents to thereby obtain PyClock.

The above reaction is preferably performed in the presence of a base which activates the 6-chloro-1-hydroxybenzotriazole and promotes the formation of the O—P bond. Representative examples of suitable bases include, without limitation, organic bases such as trimethylamine, pyridine, tributylamine, triethylamine, benzyldimethylamine, benzyltrimethylammonium hydroxide, dimethyldiethylammonium hydroxide, ethyltrimethylammonium hydroxide, methyltriethylammonium hydroxide, tetrabutylammonium hydroxide, tetrabutylphosphonium hydroxide, tetraethylammonium hydroxide, tetramethylammonium hydroxide and tetrapropylammonium hydroxide. Preferably, the base is trimethylamine.

The reaction between tris-(1-pyrrolidino)phosphonium hexafluorophosphate and 6-chloro-1-hydroxybenzotriazole is preferably carried out in an organic solvent. Representative examples of suitable organic solvents include, without limitation, dichloromethane, chloroform, carbon tetrachloride, 1,1,1,-trichloroethane, 1-chlorobutane, 1,2-dichloroethane, acetone, benzene, cyclohexane, diethyl ether, ethyl acetate, hexane, n-butyl acetate, tetrachloroethylene, tetrahydrofuran, toluene, trichloroethylene and xylene. Preferably, the solvent is dichloromethane.

In a preferred embodiment of the present invention, tris-(1-pyrrolidino)phosphonium hexafluorophosphate is obtained by converting tris-(1-pyrrolidine)phosphine oxide the corresponding phsophonium chloride salt tri-pyrrolidin-1-yl-phosphonium chloride. The conversion is preferably effected by reacting the tris-(1-pyrrolidine)phosphine oxide with $POCl_3$, in the presence of a base (e.g., dichloromethane). The chloride is thereafter replaced by the more stable anion hexafluorophosphate by reacting the tri-pyrrolidin-1-yl-phosphonium chloride with potassium hexafluorophosphate ($KPF_6$), so as to obtain tris-(1-pyrrolidino) phosphonium hexafluorophosphate.

In another preferred embodiment of this aspect of the present invention, the process further comprises purifying the obtained PyClock, so as to remove residual amounts of optional side products that are formed during the reaction, as well as unreacted starting materials and other impurities. An exemplary purification procedure is described in the Examples section that follows (see, Example 1). An exemplary process of preparing PyClock according to the present embodiments is presented in FIG. 5.

The process of preparing PyClock, according to this aspect of the present invention, typically results in highly pure final product. Thus, the purity of the obtained PyClock preferably equals to or is greater than 96%, more preferably equals to or is greater than 96.5%, more preferably equals to or is greater than 97%, more preferably equals to or is greater than 97.5% and even more preferably equals to or is greater than 98%, as determined by HPLC.

As discussed hereinabove and is further demonstrated in the Examples section that follows, the reactivity of PyClock was tested and compared to that of the known coupling agent ByBOP. PyClock has proved to be a highly reactive reagent in general and an efficient coupling agent in particular, as compared with the commonly used coupling agent, PyBOP. PyClock has further shown to be effective in synthesizing peptides containing the unnatural amino acid N-methylvaline (NMeVal), where the commonly used coupling agent had altogether failed.

Without being bound to any particular theory, it is assumed that PyClock acts as a coupling agent via a mechanism similar to that illustrated in FIG. 3, namely, by first interacting with the carboxylic acid group via the phsophonium moiety, while releasing the benzotriazole moiety; and then replacing the phsophonium moiety by the generated benzotriazole moiety so as to provide an activated form of the amino acid which readily couples to another amino acid.

Further, and without being bound to any particular theory, it is assumed that the high reactivity of PyClock, particularly as compared with PyBOP, is attributed to the presence of a chloro substituent at the benzotriazole ring.

Hence, according to another aspect of the present invention, there is provided a method of synthesizing a peptide, which is effected by sequentially coupling a plurality of amino acids, one with another, in the presence of 6-chloro-1-hydroxybenzotriazol-1-yl-N-oxy-tris(pyrrolidino)phosphonium hexafluorophosphate, which acts as a coupling agent, to thereby obtain a peptide containing the plurality of amino acids.

According to the present embodiments, the PyClock can be used as a coupling agent that promotes peptide bond formation between amino-acid and amino-acid analogues, in any of the known techniques for preparing peptides. These techniques, known to any skilled artisan, are based on the sequential and iterative reaction of natural and/or unnatural amino acids, which are optionally and preferably protected, with one another, so as to form a peptide.

As used herein, the term "peptide" encompasses a biomolecule that comprises a plurality of amino acid residues, linked one to another via a peptide bond or a modification thereof. A peptide includes at least 2 amino acid residues and up to 200 amino acid residues and even more. This term, as used herein, encompasses also polypeptides, peptidomimetics, as well as peptoids and semipeptoids which are peptide analogs, which may have, for example, modifications rendering the peptides more stable while in a body or more capable of penetrating into cells.

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Abbreviations used herein for amino acids and the designations of peptides follow the rules d the IUPAC-IUB Commission of Biochemical Nomenclature in J. Biol. Chem. 1972, 247, 977-983.

Tables 1 and 2 below list naturally occurring amino acids (Table 1) and non-conventional, modified and unnatural amino acids (Table 2) which can be used in the context of the present invention.

TABLE 1

| Amino Acid | Three-Letter Abbreviation | One-letter Symbol |
| --- | --- | --- |
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | ile | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophane | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |

TABLE 2-continued

| Non-conventional amino acid | Code | Non-conventional amino acid | Code |
|---|---|---|---|
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) | | N-(N-(3,3-diphenylpropyl) | |

TABLE 2-continued

| Non-conventional amino acid | Code | Non-conventional amino acid | Code |
| --- | --- | --- | --- |
| carbamylmethyl-glycine | Nnbhm | carbamylmethyl(1)glycine | Nnbhe |
| 1-carboxy-1-(2,2-diphenylethylamino) cyclopropane | Nmbc | | |

The peptides prepared by the method according to this aspect of the present invention are preferably linear, although cyclic forms of the peptide can also be obtained.

Cyclic peptides can either be synthesized in a cyclic form or configured so as to assume a cyclic form under desired conditions (e.g., physiological conditions).

Any of the presently known techniques for chemically synthesizing a peptide can be used in this context of the present invention. These include, for example, standard solid phase techniques including exclusive solid phase synthesis, partial solid phase synthesis methods, and fragment condensation, and classical solution synthesis. Solid phase peptide synthesis procedures are well known in the art and further described by John Morrow Stewart and Janis Dillaha Young, Solid Phase Peptide Syntheses (2nd Ed., Pierce Chemical Company, 1984).

The obtained peptides can be further purified, using, for example, preparative high performance liquid chromatography [Creighton T. (1983) Proteins, structures and molecular principles. WH Freeman and Co. N.Y.].

Other exemplary purification procedures may include hydroxyapatite, size exclusion and immobilized metal ion adsorption (IMAC) chromatography.

Suitable chromatographic media include derivatized dextrans, agarose, cellulose, polyacrylamide, specialty silicas, and the like. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like.

Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of peptides by amino groups, carboxyl groups, sulfhydryl groups, hydroxyl groups and/or carbohydrate moieties. These and other solid media are well known and widely used in the art, and are available from commercial suppliers. Selection of a particular method is preferably determined by the properties of the chosen support. See, for example, Affinity Chromatography: Principles & Methods, Pharmacia LKB Biotechnology, Uppsala, Sweden, 1988.

As is detailed in the Examples section that follows, the effectiveness of PyClock as a coupling agent has been demonstrated by the high yield of the peptide preparation process. Of particular importance is the effectiveness of PyClock when used in the syntheses of peptides that incorporate amino acid residues that are otherwise incorporated in relatively low yields and sometimes are impossible to be incorporated.

Exemplary amino acids that are considered difficult to be incorporated in common peptide syntheses include, but are not limited to, amino acids having a secondary alpha amine, amino acids having a tertiary alpha amine, amino acids having a substituted alpha carbon atom and amino acids having an amino-containing side chain.

The incorporation of amino acids that have a secondary or tertiary alpha amine into a synthetically prepared peptide is exceptionally difficult to perform, due to the hindrance of the amine that participates in the coupling reaction.

The incorporation of amino acids having a substituted alpha carbon atom also substantially affects the synthesis yield due to the stearic interactions induced by the substituent, which interfere with the coupling reaction. The incorporation of two consecutive such amino acids is even more complicated. As is well known in the art, amino acids that are substituted at the alpha carbon even by a low alkyl such as methyl are difficult to be incorporated in a peptide sequence.

The incorporation of amino acids that have an amino-containing side chain is oftentimes complicated by the unselective reaction of a coupling agent with the side chain amine group. Such an unselective reaction leads to termination of the peptide chain.

As mentioned above, the method, according to this aspect of the present invention, is therefore particularly useful for synthesizing peptides that includes one or more residues of the amino acids cited above.

As used herein throughout, the phrase "amino acid residue" describes a residue of an amino acid which forms a part of a peptide, namely, which is coupled to at least one another amino acid residue.

Thus, in embodiments of the present invention, at least one of the pluralities of amino acids that are used for synthesizing the peptide is an amino acid having a secondary alpha amine, an amino acid having a tertiary alpha amine, an amino acid having a substituted alpha carbon atom and/or an amino acid having an amino-containing side chain. The peptides prepared by this method therefore include at least one residue of such amino acids.

According to one embodiment of this aspect of the present invention, one or more of the plurality of amino acids is an amino acid having a secondary alpha amine or an amino acid having a tertiary alpha amine. According to another embodiment of the present invention, a peptide containing one or more residues of such an amino acid is obtained in a yield greater than 10%, greater than 15%, greater than 20%, greater than 25% and even greater than 30%.

According to another embodiment of the present invention, one or more of the plurality of amino acids in an amino acid having a substituted alpha carbon. In a preferred embodiment the alpha carbon is substituted by an alkyl such as methyl. An exemplary amino acid in this respect is amino isobutyric acid (aib). In a preferred embodiment, at least two such amino acids are sequentially incorporated in the peptide prepared by the method presented herein, such that the peptide comprises two such amino acids that are coupled one to another. According to another embodiment of the present invention, a peptide containing two or more residues of such an amino acid, coupled one to another is obtained in a yield greater than 70%, greater than 75%, greater than 80%, greater than 85%, greater than 90% and even greater than 95%.

According to still another embodiment of the present invention, one or more of the plurality of amino acids is an amino acid having an amine-containing side chain, such as arginine. In a preferred embodiment, at least two such amino acids are sequentially incorporated in the peptide prepared by the method presented herein, such that the peptide comprises two such amino acids that are coupled one to another. According to another embodiment of the present invention, a peptide containing one or more residues of such an amino acid is obtained in a yield greater than 60%, greater than 65%, greater than 70%, greater than 75%, greater than 80% and even greater than 85%.

In another embodiment of this aspect of the present invention, in each of the sequential attachments of the amino acids, the PyClock coupling agent is used in an amount that ranges from 0.2 mol equivalent to 5 mol equivalents relative to the molar amount of the amino acid, preferably from about 0.5 mol equivalent to 2 mol equivalents relative to the molar amount of the amino acid and more preferably a stochiometric amount of the coupling agent is used.

Using the above described method, which utilized the high reactivity and selectivity of the coupling agent presented herein, peptides compositions which comprise a high concentration of the desired peptide, namely, a peptide having the desired sequence, can be obtained. Such compositions typically have a concentration of a desired peptide which is higher than that obtained using, for example PyBOP.

Thus, according to a further aspect of the present invention there is provided a crude composition of peptides, which is synthesized in a C-terminus to N-terminus direction, and which consists essentially of a peptide having a desired amino acid sequence and a plurality of peptides having undesired amino acid sequences, which are impurities of the peptide that has the desired amino acid sequence. According to this aspect of the present invention, the concentration of the peptide having the desired amino acid sequence in the composition is at least 5% above a concentration of an identical peptide having the desired amino acid sequence in a composition of peptides being synthesized in a C-terminus to N-terminus direction using, for example, benzotriazol-1-yl-N-oxy-tris(pyrrolidino)phosphonium hexafluorophosphate (PyBOP) as a coupling agent otherwise prepared under the same conditions.

As used herein, the phrase "a peptide having a desired sequence" describes a peptide that comprises a desired sequence in terms of the order and the composition of amino acids in the peptide chain and a desired chain length in terms of the number of amino acids in the peptide chain.

The phrase "a peptide having an undesired sequence" describes a peptide that comprises a different sequence, in terms of order and composition of the amino acids in the peptide chain and a different chain length in terms of the number of amino acids in the peptide chain, as compared with a peptide having a desired sequence.

The phrase "a crude composition of peptides" describes a crude product of a peptide synthesis (in which the peptides are prepared in a C-terminus to N-terminus direction). As is well known ion the art, such a crude product is consisted of a peptide having a desired sequence, as defined herein, which is contaminated by peptides having an undesired sequence, as defined herein. Depending on the synthetic method used for preparing the peptide and the conditions and procedures employed therewithin, such a crude composition can be in a form of a solid or a solution. Solid compositions can be, for example, powdered or lyophilized. The composition can further be bound to a solid support, onto which the peptide was synthesized. Solutions may include the composition solubilized or dissolved in a liquid media Such a liquid media is typically an aqueous media, which comprises, in addition to water, various salts, buffers and the like.

In preferred embodiments of this aspect of the present invention, the concentration of the peptide having the desired amino acid sequence in the composition is at least 5%, at least 8%, at least 10%, at least 12%, at least 15%, at least 18%, at least 20%, at least 22%, at least 25%, and even at least 30% above a concentration of an identical peptide having the desired amino acid sequence in a composition of peptides being synthesized in a C-terminus to N-terminus direction using, for example, benzotriazol-1-yl-N-oxy-tris(pyrrolidino)phosphonium hexafluorophosphate (PyBOP) as a coupling agent otherwise prepared under the same conditions.

Particularly preferred crude compositions according to this aspect of the present invention are those in which the peptide having the desired amino acid sequence comprises at least one amino acid residue selected from the group consisting of a residue of an amino acid having a secondary alpha amine, a residue of an amino acid having a tertiary alpha amine, a residue of an amino acid having a substituted alpha carbon atom and a residue of an amino acid having an amino-containing side chain, as is defined and detailed hereinabove.

Further preferred crude compositions according to this aspect of the present invention are those in which the peptide having the desired amino acid sequence comprises at least two coupled amino acid residues, whereby at least one of the at least two amino acid residues is selected from the group consisting of a residue of an amino acid having a secondary alpha amine and a residue of an amino acid having a tertiary alpha amine.

Further preferred crude compositions according to this aspect of the present invention are those in which the peptide having the desired amino acid sequence comprises at least two coupled amino acid residues acids having a substituted alpha carbon atom (e.g., aib residues).

Further preferred crude compositions according to this aspect of the present invention are those in which the peptide having the desired amino acid sequence comprises at least two coupled amino acid residues acids having an amino-containing side chain (e.g., arginine).

Based on the surprising effectiveness and simplicity of production of the PyClock coupling agent described above, it has been envisioned that other, structurally related compounds, could be similarly prepared and efficiently used as coupling agents. While, as is discussed hereinabove, the superior activity of PyClock as compared with other phosphonium salts of benzotriazole used heretofore as coupling agents, may be attributed to the presence of a halogen atom on the benzotriazole moiety, the novel phsophonium salts presented herein all include such a halogen substituent.

Thus, according to an additional aspect of the present invention, there is provided a novel class of compounds which can be used as coupling agents.

The novel coupling agents presented herein can be collectively represented by the following general Formula:

Formula I wherein:

X is halo;

Y is selected from the group consisting of CR' and nitrogen, as R' is defined herein;

Z is an inorganic anion;

$R_1$-$R_6$ are each independently selected from the group consisting of hydrogen, alkyl, cycloalkyl and aryl, or, alternatively, at least one of $R_1$ and $R_2$, $R_3$ and $R_4$ and $R_5$ and $R_6$ forms a five- or six-membered carbocyclic ring; and R' is selected from the group consisting of hydrogen, alkyl and cycloalkyl.

The novel compounds presented herein are hence phosphonium salts of benzotriazoles, whereby the benzotriazole moiety is substituted by a halogen atom.

As used herein, the term "halo" describes a fluoro, chloro, bromo and iodo substituents. Preferably, the halogen atom in the compounds described herein is chloro.

The halo substituent can be at any position of the benzotriazole moiety, that is, at position 5, 6, 7 or 8 of the benzotriazole moiety. Preferably, the halogen substituent is at position 6 of the benzotriazole moiety.

Preferred phosphonium salts, according to the present invention are those wherein at least one of $R_1$ and $R_2$, $R_3$ and $R_4$ and $R_5$ and $R_6$ forms a five- or six-membered carbocyclic ring. More preferred compounds are those wherein each of $R_1$ and $R_2$, $R_3$ and $R_4$ and $R_5$ and $R_6$ forms a five- or six-membered carbocyclic ring. Most preferred compounds are those wherein each of $R_1$ and $R_2$, $R_3$ and $R_4$ and $R_5$ and $R_6$ forms a five-membered carbocyclic ring, whereby the formed carbocyclic rings are identical.

As used herein, the phrase "carbocyclic ring" describes an all-carbon monocyclic or fused ring (i.e., rings which share an adjacent pair of carbon atoms) group wherein each of the rings can have either a completely conjugated pi-electron system or a non-conjugated or partially-conjugated pi-electron system. This phrase therefore encompasses cycloalkyls and aryls, as these terms are defined herein.

Preferably the carbocyclic ring is a cycloalkyl and more preferably it is a saturated cycloalkyl such as cyclopentane. Thus, the phsophonium moiety in the compounds presented herein preferably includes a positively charged phosphor atom having 3 pyrrolidine moieties attached thereto.

The anion in the phosphonium salts described herein, represented as $Z^-$ in general Formula I, is an inorganic anion such as, for example, halide, hexahalophosphate, tetrahaloborate, trihalomethanesulfonate and bis(trihalomethylsulfonyl)imide.

As used herein, the term "halide" describes a negatively charged chloride, fluoride, bromide and iodide.

The term "hexahalophosphate" describes a $PL_6^-$ group, wherein L is a halogen atom, as described above.

The term "tetrahaloborate" describes a $BL_4^-$ group, wherein L is a halogen atom, as described above.

The term "trihalomethanesulfonate" describes a $CX_3SO_2^-$ group, wherein L is a halogen atom, as described above.

The term "bis(trihalomethylsulfonyl)imide" describes a $[N(SO_2CL_3)_2]^-$ group, wherein L is a halogen atom, as described above.

A preferred anion according to the present embodiments is a hexahalophosphate, and, more preferably, it is hexafluorophosphate. As is known in the art, salts including hexafluorophosphate are typically stable and non-hygroscopic solids and are thus easy to handle.

As shown in Formula I above, the compounds presented herein can be either benzotriazoles, where Y in Formula I is CR', or N-benzotriazole, wherein Y is N.

Similar to PyClock, the novel compounds presented herein are readily prepared by reacting a reactive derivative of a halogenated benzotriazole with a corresponding phosphonium salt. Hence, according to still an additional aspect of the present invention, there is provided a process of preparing the novel coupling agents having the general Formula I presented hereinabove. The process, according to this aspect the process is effected by providing a compound having the general Formula II:

Formula II wherein:

$R_1$-$R_6$ are each independently selected from the group consisting of hydrogen, alkyl, cycloalkyl and aryl, or, alternatively, at least one of $R_1$ and $R_2$, $R_3$ and $R_4$ and $R_5$ and $R_6$ forms a five- or six-membered carbocyclic ring, as detailed hereinabove; and Z is an anion, as is detailed hereinabove;

providing a compound having the general Formula III:

Formula III wherein:

X is a halogen atom, preferably chloro;

Y is selected from the group consisting of CR' and nitrogen; and

T is selected from the group consisting of hydrogen, alkyl, and cycloalkyl; and reacting the compound having the general Formula II and the compound having the general Formula III, thereby obtaining the compound having general Formula I.

As in the process of preparing PyClock, the reaction between the compound having Formula II and the compound having Formula III is preferably performed in the presence of a base and in an organic solvent.

The compound having the general Formula II can be obtained by providing a compound having the general Formula IV:

Formula IV wherein W is selected from the group consisting of oxygen and sulfur;

converting the compound having said general Formula IV to a phosphonium halide salt thereof; and reacting the phosphonium halide with the anion denoted Z to thereby obtain the compound having the general Formula II.

The novel class of phosphonium salts of benzotriazoles presented herein, by being structural analogs of PyClock, can be similarly used as highly efficient coupling agents and particularly as efficient coupling agents for use in the preparation of peptides.

Thus, according to a further aspect of the present invention, there is provided a method of synthesizing peptides which utilizes a compound having the general Formula I as a peptide coupling agent. The method, according to this aspect of the present invention, is effected using any of the synthesis techniques and amino acids described hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Preparation of 6-chloro-1-hydroxybenzotriazol-1-yl-N-oxy-tris(pyrrolidino)phosphonium hexafluorophosphate (PyClock)

HPLC Analysis:

HPLC analysis was conducted using an RP-18 column (250×4); a mobile phase of 90:10 0.1% TFA in ACN:0.1% TFA/$H_2O$; and a flow rate of 2 ml/minute, following the mixture at a wavelength of 254 nm. Retention time of the final product was 6.2 minute.

Preparation of tris-(1-pyrrolidino)phosphonium hexafluorophosphate: A solution of tris-(1-pyrrolidine)phosphine oxide (32.3 grams) in dichloromethane (17.5 ml) was slowly added during 20 minutes to a cooled (water-ice bath) solution of $POCl_3$ (19.2 grams) in dichloromethane (17.5 ml), under nitrogen atmosphere, while maintaining the reaction mixture temperature below 30° C. The reaction mixture was further stirred for 1 hour at room temperature and attained a red-pink color.

The reaction mixture was then cooled to 5° C. for 10 minutes, and a suspension of the $KPF_6$ (46 grams) in water (200 ml) was added while rigorously stirring the reaction mixture maintaining its temperature at 5-10° C. The reaction mixture was further stirred at room temperature for 30 minutes.

The phases were thereafter separated, and the aqueous phase was washed with 2×50 ml dichloromethane. The organic phases were combined and washed with 3×100 ml water, dried over $MgSO_4$, and filtrated. The filtrate was evaporated to dryness under reduced pressure to obtain 49.0 grams of tris-(1-pyrrolidino)phosphonium hexafluorophosphate as a slightly colored solid (93% yield).

Preparation of 6-chloro-1-hydroxybenzotriazol-1-yl-N-oxy-tris(pyrrolidino)phosphonium hexafluorophosphate: A solution of 6-chloro-1-hydroxybenzotriazole (Cl-HBOT, 70 grams, 0.117 moles) and triethylamine (16.5 ml, 0.117 moles) in dichloromethane (70 ml) was added dropwise during 20 minutes to a stirred solution of tris-(1-pyrrolidino) phosphonium hexafluorophosphate (49 grams, 0.117 moles) in acetone (500 ml) while maintaining the reaction mixture temperature below 20° C. Stirring was continued for 3 hours, during which a precipitate (triethyl ammonium HCl salt) was formed. The precipitate was filtered off and the filtrate was evaporated to dryness under reduced pressure.

In order to remove the 6-Cl HOBT side product formed during the reaction, the solid residue obtained was dissolved in 700 ml dichloromethane, $MgSO_4$ (10 grams) was added to solution while stirring during 15 minutes, and the resulting suspension was stirred for an additional hour. The suspension was then filtered, and the filtrate was evaporated to dryness under reduced pressure to give 42 grams of 6-chloro-1-hydroxybenzotriazol-1-yl-N-oxy-tris(pyrrolidino)phosphonium hexafluorophosphate as a solid (65% yield) having 98.5% purity (containing 1.4% 6-Cl-HBOT) as determined by HPLC.

Figure 5:
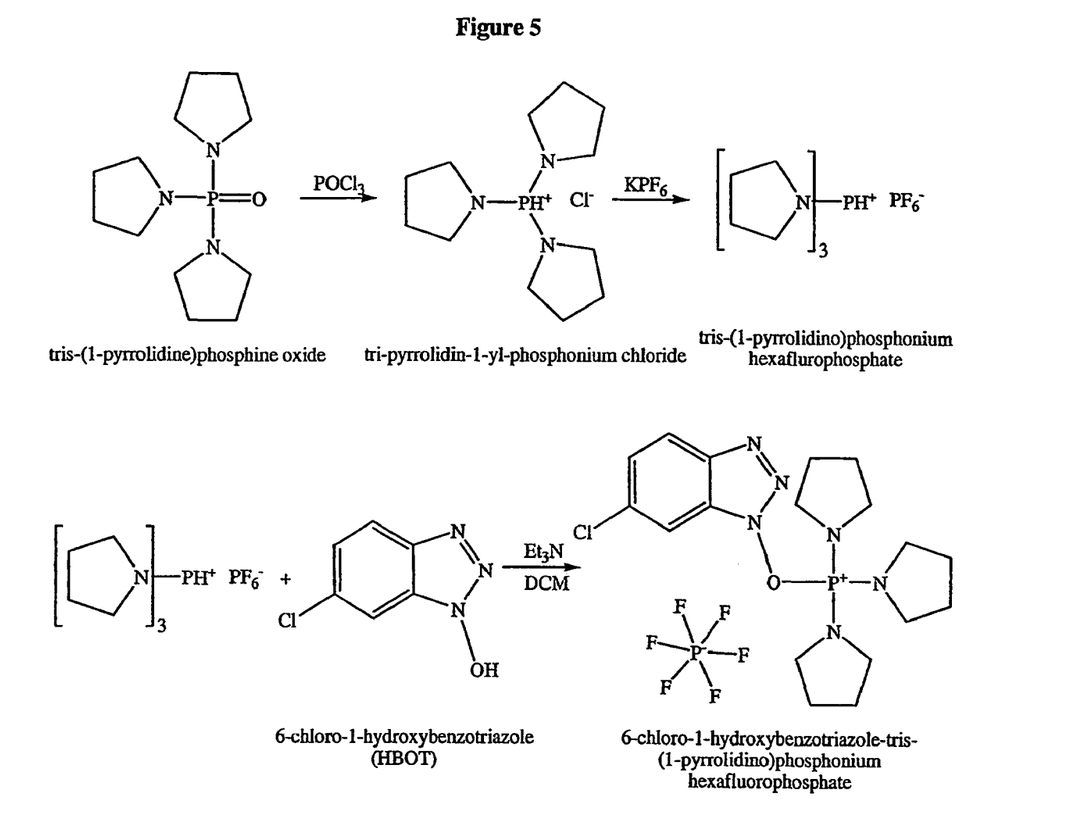
FIG. 5 presents a scheme illustrating an exemplary process of preparing 6-chloro-1-hydroxybenzotriazol-1-yl-N-oxy-tris(pyrrolidino)phosphonium hexafluorophosphate, a preferred peptide coupling agent according to the present invention.

The overall synthesis of 6-chloro-1-hydroxybenzotriazol-1-yl-N-oxy-tris(pyrrolidino)phosphonium hexafluorophosphate is illustrated in FIG. 5.

Example 2

Comparative Reactivity Studies

The stability of 6-chloro-1-hydroxybenzotriazol-1-yl-N-oxy-tris(pyrrolidino)phosphonium hexafluorophosphate (PyClock), which may serve as a criteria for its reactivity and efficiency as a peptide coupling agent (less stable means more reactive), was studied by way of comparison to the widely used commercially available coupling agent benzotriazole-1-yl-oxy-tris-pyrrolidino-phosphonium hexafluorophosphate (PyBOP).

Materials and Experimental Methods:

6-chloro-1-hydroxybenzotriazol-1-yl-N-oxy-tris(pyrrolidino)phosphonium hexafluorophosphate (PyClock) was prepared as described in Example 1.

HPLC analysis was carried out on a Waters instrument 996 photodiode array detectors equipped with the waters 2695 separation module and the millennium software, using HPLC reversed phase symmetry columns C18 4.6×150 mm, 5 µm (obtained from Waters, Ireland). U.V detection was performed at 220 nm. A linear gradient mobile phase starting with $CH_3CN$ (containing 0.036% TFA) and ending with $H_2O$ (containing 0.045% TFA) was used at a flow rate of 1.0 ml/minute.

Stability Assays:

All the stability assays were carried out using a 0.05 M solution of the coupling agent in DMF.

Samples were taken at different time points and were evaluated by analytical HPLC. The appearance of the breakdown products 1-hydroxy-6-chlorobenzotriazole (Cl-HOBt) for PyClock and 1-hydroxy-benzotriazole (HOBt) for PyBOP served as an indication of the stability thereof.

Table 3 below presents representative results obtained in these studies, reported in peak areas percentages.

TABLE 3

|  | PyClock |  | PyBOP |  |
| --- | --- | --- | --- | --- |
| Time | Cl-HOBt | PyClock | HOBt | PyBOP |
| 6 hours | 31.2% | 68.8% | 22.1% | 77.9% |
| 10 hours | 55.2% | 44.8% | 36.0% | 64.0% |

These results clearly show that PyClock is less stable and hence more reactive more reactive than the presently known peptide coupling agent ByBOP.

Additional stability studies were performed in the presence of the tertiary amine N,N-diisopropylethylamine (DIEA), which is used as a typical base in peptide syntheses. Thus, DIEA (2 mol equivalents) was added to each of the tested solutions, and the appearance of the breakdown products described above over time was monitored. Table 4 below presents representative results obtained in these studies, reported in peak areas percentages.

TABLE 4

|  | PyClock |  | PyBOP |  |
| --- | --- | --- | --- | --- |
| Time | Cl-HOBt | PyClock | HOBt | PyBOP |
| 1 hour | 87.6% | 12.4% | 81.6% | 18.4% |

The results clearly show that PyClock is more reactive in the presence of a tertiary amine than its commercially available counterpart.

Example 3

Comparative Solid-Phase Peptide Syntheses

The reactivity of PyClock as a coupling agent in solid-phase peptide syntheses was tested and compared with that of PyBOP. To this end, solid phase syntheses of various peptides, which are considered difficult to prepare by conventional synthetic approaches, were performed.

Materials and Experimental Methods:

6-chloro-1-hydroxybenzotriazol-1-yl-N-oxy-tris(pyrrolidino)phosphonium hexafluorophosphate (PyClock) was prepared as described in Example 1.

The following Fmoc-N-protected amino acids were used: tyrosine (Fmoc-L-Tyr(tBu)-OH), N-methylvaline (Fmoc-L-NMeVal-OH), aminoisobutyric acid (Fmoc-Aib-OH), phenylalanine (Fmoc-L-Phe-OH), leucine (Fmoc-L-Leu-OH) and arginine (Fmoc-L-Arg(Pbf)-OH).

Peptide Syntheses:

Solid phase peptide syntheses were carried out in polypropylene syringes (10 ml) fitted with a polyethylene porous disc, using general Fmoc chemistry, as follows:

All procedures were performed at 25° C. Each cycle included Fmoc deprotection, washing, coupling an amino acid to the resin-bound peptidyl in the presence of the tested coupling agent and washing.

Fmoc deprotection was carried out using 20% piperidine in DMF (1×1 minute, 2×10 minutes).

Washings between repetitive cycles of deprotection and coupling were carried out using DMF (5×1 minutes, 10 ml solvent per 1 gram of resin).

5 molar equivalents of a Fmoc-protected amino acid, 5 molar equivalents of the tested coupling agent and 15 molar equivalents of N,N-diisopropylethylamine (DIEA) were reacted with 1 molar equivalent of a resin in each cycle.

Thus, DMF (0.2 ml) was added to a mixture of a first Fmoc-protected amino acid, a coupling agent and DIEA and after 5 minutes the resulting mixture was added to the Rink resin (50 mg, 0.66 mmol/gram). Upon washing, Fmoc deprotection and washing, a mixture containing a second Fmoc protected amino acid and a coupling agent was reacted with the resin, as described above. This procedure was repeated until the peptide synthesis was completed.

Upon completion, the peptide was cleaved from the resin by treatment with neat TFA for 1 hour, to remove residual Fmoc and other protection groups. Methyl-t-butylether was then added to the resulting peptide and the resulting solid precipitate was isolated by means of centrifugation. Precipitation was performed trice and the isolated peptide was then subjected to lyophilization.

Table 5 below presents the results of the comparative solid-phase peptide synthesis using PyClock, the peptide coupling agent of the present invention, and PyBOP, by reporting the overall yield of synthesis for each peptide coupling agent.

TABLE 5

| Peptide | PyClock | PyBOP |
| --- | --- | --- |
| H-Tyr-NMeVal-Phe-Leu-NH$_2$ | 11.4% | null |
| H-Tyr-Aib-Aib-Phe-Leu-NH$_2$ | 96.6% | 83.5% |
| H-Tyr-Arg-Arg-Phe-Leu-NH$_2$ | 84.7% | 74.8% |

The result clearly show that the peptide coupling agent of the present invention is more effective in promoting the formation of an amide bond between various naturally occurring and unnatural amino acids, as compared with a commercially available peptide coupling agent.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A compound having the general formula I:

wherein:

Z is an inorganic anion; and $R_1$-$R_6$ are each independently selected from the group consisting of hydrogen, alkyl, cycloalkyl and aryl, or, alternatively, at least one of $R_1$ and $R_2$, $R_3$ and $R_4$ and $R_5$ and $R_6$ forms a five- or six-membered carbocyclic ring.

2. The compound of claim 1, wherein each of $R_1$ and $R_2$, $R_3$ and $R_4$ and $R_5$ and $R_6$ forms a five- or six-membered carbocyclic ring.

3. The compound of claim 2, wherein each of $R_1$ and $R_2$, $R_3$ and $R_4$ and $R_5$ and $R_6$ forms a five-membered carbocyclic ring.

4. The compound of claim 1, wherein said anion is selected from the group consisting of hexahalophosphate, tetrahaloborate, trihalomethanesulfonate and bis(trihalomethylsulfonyl)imide.

5. The compound of claim 4, wherein said anion is hexafluorophosphate.

6. The compound of claim 3, wherein said each of said $R_1$ and $R_2$, $R_3$ and $R_4$ and $R_5$ and $R_6$ forms a pyrrolidine.

7. The compound of claim 6, wherein said anion is hexafluorophosphate.

8. The compound of claim 1, being 6-chioro-1-hydroxybenzotriazol-1-yl-N-oxy-tris(pyrrolidino)phosphonium hexafluorophosphate (PyClock).

* * * * *